(12) United States Patent
Chambers

(10) Patent No.: US 10,595,992 B2
(45) Date of Patent: Mar. 24, 2020

(54) DEVICES, SYSTEMS AND METHODS FOR CARDIAC TREATMENT

(71) Applicant: 4C Medical Technologies, Inc., Brooklyn Park, MN (US)

(72) Inventor: Jeffrey W. Chambers, Maple Grove, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 707 days.

(21) Appl. No.: 15/047,877

(22) Filed: Feb. 19, 2016

(65) Prior Publication Data
US 2016/0242905 A1     Aug. 25, 2016

Related U.S. Application Data

(60) Provisional application No. 62/118,797, filed on Feb. 20, 2015.

(51) Int. Cl.
    *A61F 2/24*               (2006.01)

(52) U.S. Cl.
    CPC ............ *A61F 2/2418* (2013.01); *A61F 2/243* (2013.01); *A61F 2/2409* (2013.01);
(Continued)

(58) Field of Classification Search
    CPC .... A61F 2/2409; A61F 2/2412; A61F 2/2418; A61F 2/243; A61F 2/2436; A61F 2/2439; A61F 2/2487
See application file for complete search history.

(56) References Cited

U.S. PATENT DOCUMENTS

| 5,776,188 A | 7/1998 | Shepherd et al. |
| 6,371,983 B1 | 4/2002 | Lane |

(Continued)

FOREIGN PATENT DOCUMENTS

| JP | 2012508033 | 4/2012 |
| WO | 2007/025028 | 3/2007 |
| WO | 2009/132187 | 10/2009 |

OTHER PUBLICATIONS

International Preliminary Report on Patentability, dated Aug. 31, 2017, for PCT Application No. PCT/US16/018644, filed Feb. 19, 2016.
(Continued)

*Primary Examiner* — Julie A Szpira
(74) *Attorney, Agent, or Firm* — Barnes & Thornburg LLP; Jeffrey R. Stone

(57) ABSTRACT

A device for providing cardiac treatment at the left atrium of a patient's heart. The device includes a retention body and a prosthetic valve. The retention body has a shape that can be manipulated between a collapsed state and a normal or expanded state. First and second openings are defined at one side of the retention body, and a lower opening is defined at an opposite side. The prosthetic valve is carried by the retention body at the lower opening. The retention body is configured to engage a substantial portion of an interior surface of the left atrium, securing the prosthetic valve at a desired location relative to a native mitral valve (e.g., within the mitral valve or slightly spaced from the mitral valve). The first and second openings are sized and shaped so as to permit blood flow from the pulmonary veins into the interior region.

50 Claims, 15 Drawing Sheets

(52) U.S. Cl.
CPC .......... *A61F 2/2412* (2013.01); *A61F 2/2436* (2013.01); *A61F 2/2439* (2013.01); *A61F 2/2487* (2013.01)

(56) References Cited

U.S. PATENT DOCUMENTS

| | | |
|---|---|---|
| 2006/0025855 A1 | 2/2006 | Lashinski et al. |
| 2008/0027268 A1 | 1/2008 | Buckner et al. |
| 2010/0036479 A1* | 2/2010 | Hill ...................... A61F 2/2418 623/1.15 |
| 2011/0112632 A1 | 5/2011 | Chau et al. |
| 2011/0307003 A1* | 12/2011 | Chambers ........ A61B 17/12122 606/200 |
| 2014/0031928 A1 | 1/2014 | Murphy et al. |
| 2014/0277422 A1 | 9/2014 | Ratz et al. |

OTHER PUBLICATIONS

4C Medical Technologies, Inc., PCT/US16/18644 filed Feb. 19, 2016, "The International Search Report and the Written Opinion of the International Searching Authority, or the Declaration", dated May 6, 2016.

Extended European Search Report issued in related European Patent Application No. 16753133.4, dated Jan. 25, 2019.

* cited by examiner

DEVICES, SYSTEMS AND METHODS FOR CARDIAC TREATMENT

CROSS-REFERENCE TO RELATED APPLICATIONS

This application claims priority under 35 U.S.C. § 119 to provisional application Ser. No. 62/118,797, filed Feb. 20, 2015, which is herein incorporated by reference in its entirety.

FIELD OF THE INVENTION

The present disclosure generally relates to systems and methods for cardiac surgical repairs. More particularly, it relates to systems and methods for securing a prosthetic valve relative to a chamber of the heart, such as the left atrium, as well as other treatments of the cardiac chamber.

BACKGROUND OF THE INVENTION

The mitral valve regulates blood flow between the left atrium and the left ventricle. Mitral regurgitation (MR), which is also known as mitral insufficiency, is a common heart valve disorder. MR is a disorder of the heart in which the mitral valve does not close properly when the heart pumps out blood. When MR is present, blood leaks backwards through the mitral valve when the heart contracts. This reduces the amount of blood that is pumped out to the body. A defective mitral valve can be repaired or replaced with a prosthetic mitral valve. Prosthetic mitral valves can take various forms, and generally employ either a tissue-based valve structure (i.e., bioprosthesis) or a mechanical valve. Regardless, implantation of a prosthetic mitral valve entails securing the prosthesis to the tissue of the native valve either by sutures (e.g., open heart procedure) or by a stent component of the prosthesis that bears directly against the native valve annulus or other valve anatomy (e.g., transcatheter procedure). Open heart procedures are highly traumatic to the patient. While transcatheter techniques are less invasive, possible migration of the prosthetic valve can be a concern.

In light of the above, a need exists for systems and methods for securing a prosthetic valve relative to a chamber of the heart, such as the left atrium, and optionally for preventing formation of blood clots in the left atrium.

SUMMARY OF THE INVENTION

It is therefore a principle object, feature, and/or advantage of the disclosure to overcome deficiencies in the art.

It is another object, feature, and/or advantage of the disclosure to provide a totally or near-totally percutaneous implant for replacement of a deficient mitral valve.

It is yet another object, feature, and/or advantage of the disclosure to provide an all venous implant for valve replacement.

It is still another object, feature, and/or advantage of the disclosure to provide a valve implant that anchors in place such that there is mitigation of movement or embolism.

It is a further object, feature, and/or advantage of the disclosure to provide a valve implant that mitigates perivalvular leak.

It is still a further object, feature, and/or advantage of the disclosure to provide a valve implant that anchors within the left atrium of the heart.

These and/or other objects, features, and advantages of the present invention will be apparent to those skilled in the art. The present invention is not to be limited to or by these objects, features and advantages. No single embodiment need provide each and every object, feature, or advantage.

Some aspects in accordance with principles of the present disclosure relate to a device for providing cardiac treatment of a patient's heart. The device includes a retention body and a prosthetic valve. The retention body has a basket-like shape in a normal or expanded state. The basket-like shape defines an interior region. A lower opening is defined at a side of the retention body. The prosthetic valve is carried by the retention body at or adjacent the lower opening. The retention body is sized and shaped to engage or contact a substantial portion of an interior surface of a chamber of the patient's heart, securing the prosthetic valve at a desired location relative to a native valve (e.g., within the native valve or slightly spaced from the native valve). In some embodiments, the retention body further forms first and second openings opposite at a side opposite the lower opening. The first and second openings are sized and shaped so as to permit blood flow from the ostiums associated with the chamber into the interior region. For example, in some embodiments, the device is configured for providing cardiac treatment at the left atrium, and the first and second openings are sized and located to be open to left pulmonary vein ostiums and right pulmonary vein ostiums, respectively. In some embodiments, the retention body further includes a liner or cover. In related embodiments, the liner or covering extends across the left atrial appendage upon final implant.

Still other aspects of the disclosure include a cuff or skirt around at least a portion of the body to mitigate leakage. The body of the device can comprise or otherwise include a compliant material such that compression and expansion of the device aid in holding the device in place for a greater number of patients due to the variations in size of the native valves, while also providing for movement of the device to contract and expand with the movements of the heart without causing further damage.

The device can be delivered percutaneously, such that it is a venous implant. A delivery device, such as a catheter, can be utilized to transport the implant device to the heart where it can be anchored within the left atrium and anchored in place. Such a delivery device or apparatus can hold the implant in a collapsed stated until such time that it is allowed to expand in the atrium to aid in holding itself in place.

Figure 1A:
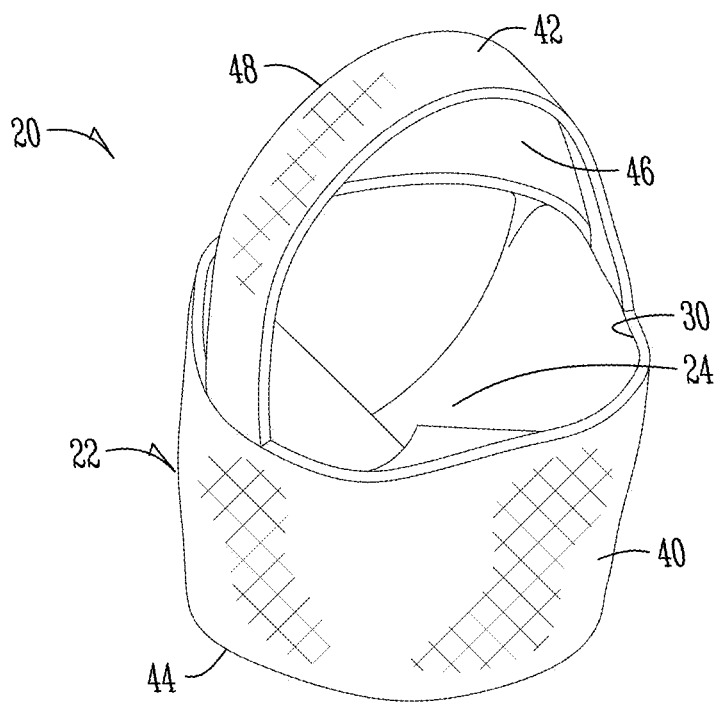
FIG. 1A is a perspective view of an implantable device in accordance with principles of the present disclosure and configured for implantation within a left atrium.

Various embodiments of the invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENTS

Figure 1B:
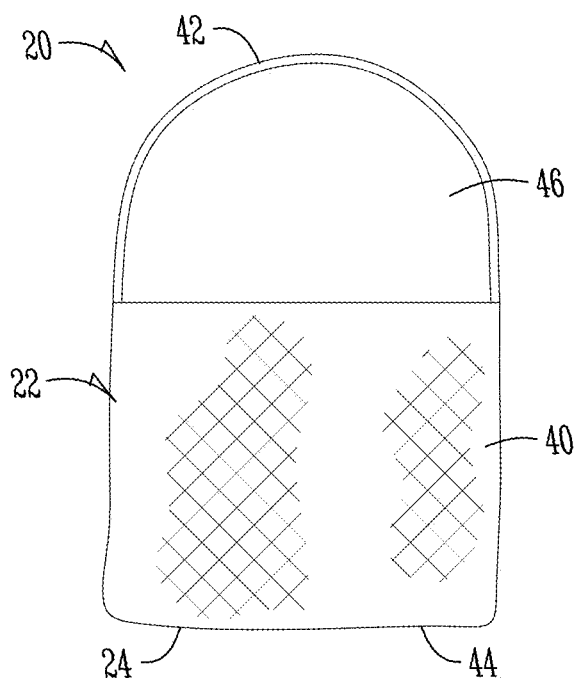
FIG. 1B is a side elevation view of the device of FIG. 1A.
Figure 1C:
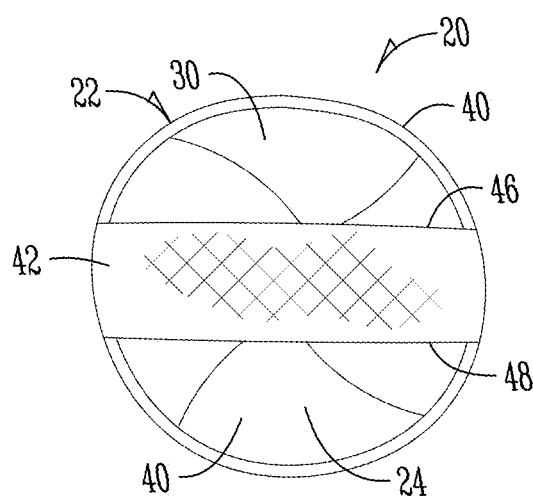
FIG. 1C is a top plan view of the device of FIG. 1A.

One embodiment of an implantable device 20 in accordance with principles of the present disclosure for repairing a defective valve is shown in FIGS. 1A-1C. As described below, the device 20 can be configured for placement at the left atrium for repairing a defective mitral valve. Alternatively, the devices of the present disclosure can be configured for placement at other chambers of the heart, such as at the right atrium for repair of a tricuspid valve. Thus, while the descriptions below describe left atrium/mitral valve applications, the present disclosure should not be construed as being limited to the left atrium/mitral valve. The device 20 includes a retention body 22 and a prosthetic valve 24. In general terms, the retention body 22 retains the prosthetic valve 24 and is expandable from a collapsed state (described below) to the expanded state of FIGS. 1A-1C. In the expanded state, the retention body 22 can have a dome-like or basket-like shape, configured to match a size, shape, and contour of an interior surface of the interior left atrium (or other chamber of the heart). As will be understood, the retention body 22 may take various other forms as well, while still complying with aspects of the present disclosure. Thus, the retention body 22 serves to at least assist in securing the prosthetic valve 24 relative to the native mitral valve by engaging the interior surface of the left atrium. According to some aspects of the disclosure, the device 20 optionally further serves as a coating or lining on the interior surface of the left atrium, thereby preventing blood clots from forming on the anatomical surface. For example, the device 20 can work with or in place of or in combination with the implantable device as shown and described in U.S. Pat. No. 8,828,043, which includes common inventorship to the present disclosure and which is hereby incorporated by reference in its entirety. As is understood, the device of the '043 patent is useful in mitigating the formation of blood clots. For reasons made clear below, the retention body 22 optionally forms or defines one or more openings sized and located to accommodate various anatomical structures associated with the chamber, such as the left atrium.

The retention body 22 can be formed of various biocompatible materials appropriate for atraumatic contact with cardiac tissue, and in some embodiments is, or is akin to, a conventional stent configuration (a series of interconnected wires, braids or struts). The stent structure of the retention body 22 can be formed of a metal, a metal alloy (e.g., Nitinol), plastic, or bioabsorbable material as are known to those of skill in the art. The retention body 22 can have a shape memory attribute whereby the retention body 22 can be forced to the collapsed state and upon transitioning to the expanded (or normal) state of FIGS. 1A-1C, the retention body self-retains the expanded state. In some embodiments, the construction of the retention body 22 inherently provides a self-expanding attribute, self-expanding from the collapsed state to or toward the expanded state. In other embodiments, the retention body 22 is configured to be expanded by a balloon or other inflation mechanism from the collapsed state to, or toward, the expanded state. Regardless, in some constructions the retention body 22 is readily collapsible from the expanded state of FIGS. 1A-1C, and can be repeatedly transitioned between the expanded and collapsed states.

Further, as will be understood, the expanding structure of the retention body 22 can provide additional advantages. For example, having the body comprise a compliant or otherwise expanding material (e.g., springs or spring-like material) will allow the implant device 20 to be sized such that it can fit with heart regions of various sizes. Such a material can be a memory material or include a shape memory. This will allow a single or few devices to be utilized in patients without having to specifically size the device to the patient's heart, such as to the size of the left atrium. Still further, the elasticity of the device body 22 will allow for the device to expand and contract while positioned within the heart, such that the implant device is movable during normal activities of the patient.

Due to the stent or stent-like construction, the retention body 22 defines an open interior region 30 (referenced generally). A shape of the retention body 22 (in the normal or expanded state) can be viewed as including a base section 40 and a shoulder section 42. The shoulder section 42 may also be referred to as an upper support member. This includes the entire member or a portion thereof. As will be understood, an upper support member 42 may not be directly connected to the retention body 22 in all forms, and instead may include one or more intermediate members therebetween to provide additional aspects to the device 20. The open interior region 30 is collectively defined by the base and shoulder sections 40, 42. The base section 40 has a ring-like shape or format, and terminates at a lower opening 44. The prosthetic valve 24 is attached to the base section 40 at or adjacent the lower opening 44, such that the prosthetic valve 24 is fluidly open or fluidly connected to the interior region 30. The shoulder section 42 projects from a side of the base section 40 opposite the lower opening 44, and has an arch-like shape. The shape of the shoulder section 42 optionally establishes opposing, first and second openings 46, 48 that are both open to the interior region 30.

In some embodiments, the retention body 22 can further include a coating or liner covering the stent. The liner can be a fabric, polymer, metal mesh, braided material, Gortex®, Teflon®, silicon, or other such material having the appropriate properties such as biological material or tissue. For example, amnion tissue can be employed, and can be variously modified or unmodified form of amnion tissue such as non-cryo amnion tissue, solubilized amnion tissue, amnion tissue fabric, chemically modified amnion tissue, amnion tissue treated with radiation, amnion tissue treated with date, or a combination thereof. Materials such as polymer, placental tissue, pericardium tissue, small intestine submucosa can also be used, alone or in combination with the amnion tissue. The tissue can be attached to the inside, the outside, both inside and outside, or complete encapsulation of a scaffolding of the retention body 22. In some constructions, at least part of the covering or lining of the retention body 22 (e.g., as applied to a scaffolding of the retention body 22) comprises a plurality of layers of tissue, such as a plurality of layers of amnion tissue. To prevent blood clot formation, the retention body 22 is optionally coated with an anti-thrombotic material or medication in some embodiments. In other embodiments, the retention body 22 is configured to promote endothealization with cardiac tissue, effectively resulting in a modified heart wall lining. Still further, and as will be understood, the body 22 can comprise a compliant and/or elastic structure such that it can be deformed, expanded, contracted, or otherwise manipulated such that it will revert to its original or near original configuration when positioned within the patient's heart chamber.

The prosthetic valve 24 can assume a wide variety of forms as known in the art for replacing and/or assisting a native mitral valve. The prosthetic valve 24 can include a bioprosthetic valve (e.g., including one or more tissue leaflets, such as bovine, porcine, equine leaflet(s), etc.). In other embodiments, the prosthetic valve 24 can include a mechanical valve as known in the art. In some embodiments, the leaflet structure(s) of the prosthetic valve 24 can be attached directly to the retention body 22 (e.g., can be sewn to the stent structure of the retention body 22). In other embodiments, the prosthetic valve 24 can include one or more support bodies that retain the leaflet(s) and that are attached to the retention body 22. For example, the prosthetic valve 24 can include a stent or similar structure (apart from the stent of the retention body) maintaining the leaflet (s); the valve stent can, for example, include or form commissural posts as is known in the art. The valve stent can optionally be covered by a cloth or similar material covering, and is attached (e.g., sewn) to the retention body 22.

Figure 2A:
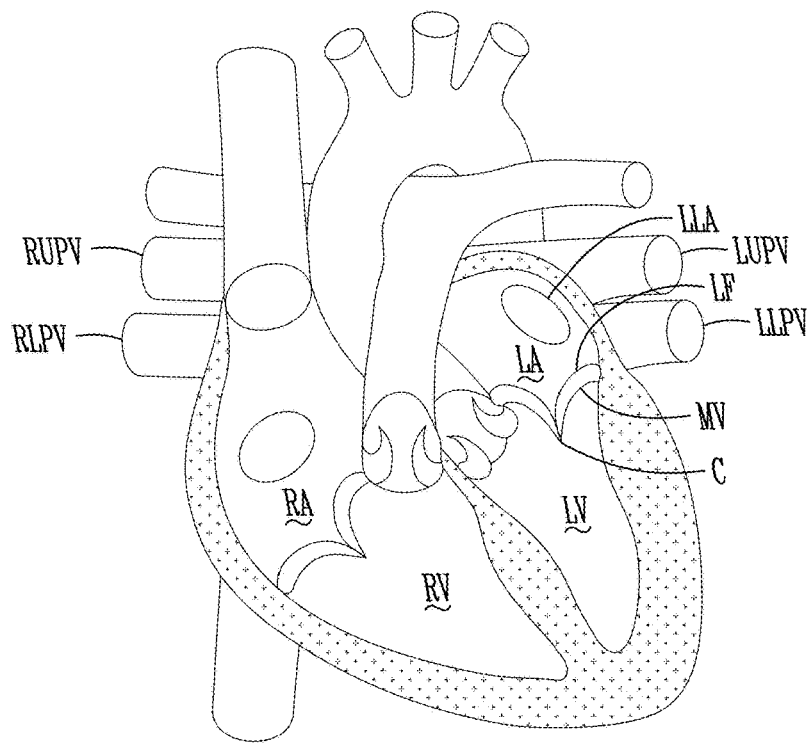
FIG. 2A is a representation of portions of a human heart.
Figure 2B:
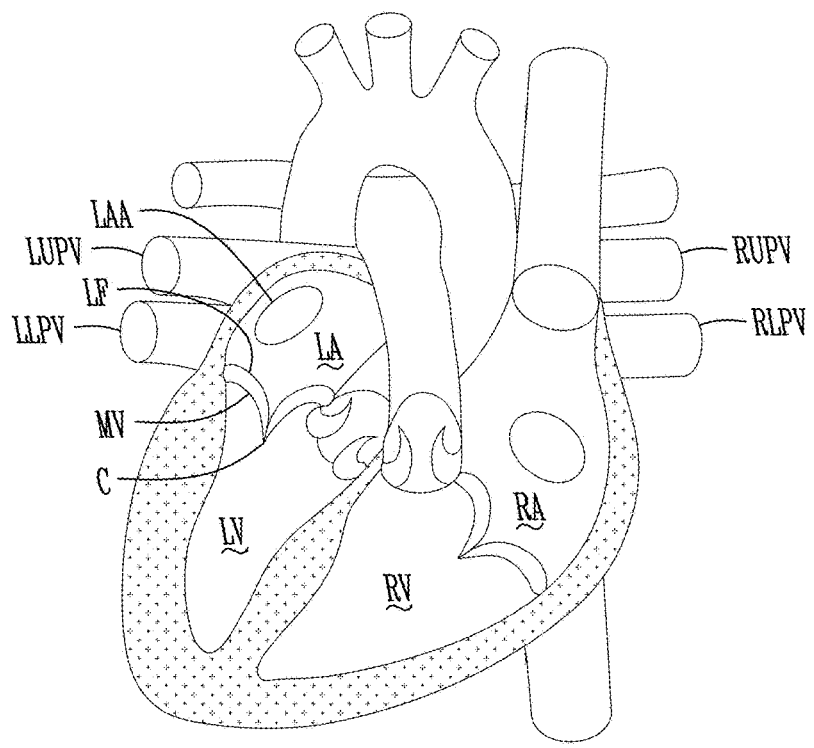
FIG. 2B is another representation of a human heart.

As indicated above, the dome-like or basket-like shape of the retention body 22 generally coincides with a size and shape of the interior left atrium in some embodiments. In this regard, FIGS. 2A and 2B provide simplified representations of portions of the human heart, including the left atrium (LA), the left ventricle (LV), the right atrium (RA), and the right ventricle (RV). Ostiums or roots of the upper and lower left pulmonary veins (LUPV, LLPV) originating at the left atrium LA wall are also reflected, as are the ostiums or roots of the upper and lower right pulmonary veins (RUPV, RLPB). The mitral valve (MV) regulates blood flow from the left atrium LA to the left ventricle LV, and includes leaflets (LF) supported by chordae tendineae (C). Finally, the left atrial appendage (LAA) in the left atrium LA is also identified.

Figure 3A:
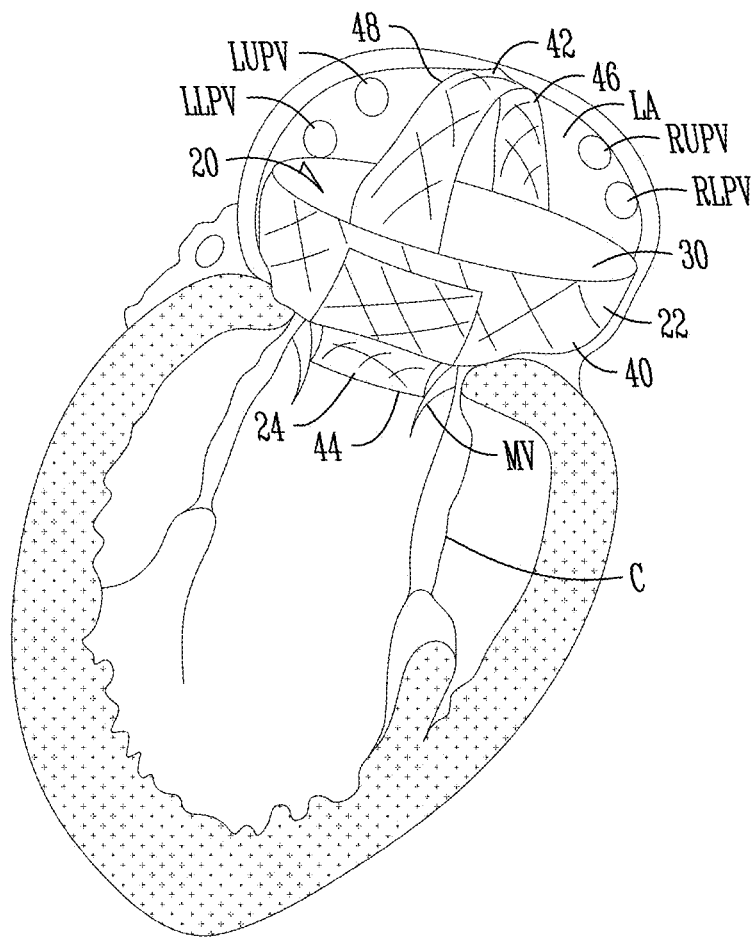
FIG. 3A is a simplified view of one arrangement of a device implanted within a left atrium portion of the anatomy of FIGS. 2A and 2B in accordance with principles of the present disclosure.

With the above anatomy in mind, FIG. 3A illustrates, in simplified form, implantation of a device 20 within the left atrium LA in accordance with some embodiments of the present disclosure. In the normal or expanded state, the retention body 22 is in direct, intimate contact with (and covers) at least a majority of a surface area of the interior surface of the left atrium LA, serving to at least assist in holding the device 20 in place, optionally providing the primary source of affixation. The device 20 is substantially self-retaining relative to the left atrium LA due to an outward or expanding bias of the retention body 22. As disclosed, this also allows for the contraction of the implant device 20 during normal activities of the patient while mitigating the risk of movement or other unwanted dislodging of the implant while positioned in the heart valve. In other embodiments, one or more tissue anchors or similar structures can be provided that intimately retain the retention device 20 against the interior surface of the left atrium LA.

The retention body 22 is sized and shaped such that upon final implant, the base section 40 extends across or covers the left atrial appendage LAA. The shoulder section 42 is in contact with the interior surface of the left atrium LA, and projects "above" a spatial location of the left atrial appendage LAA. However, the retention body 22 does not necessarily interfere with requisite blood flow from the pulmonary veins LUPV, LLPV, RUPV, and RLPV into the left atrium LA. Instead, the retention body 22 is sized and shaped such that upon final implant, the first opening 46 is open to both of the left pulmonary veins LUPV, LLPV, and the second opening 48 is open to both of the right pulmonary veins RUPV, RLPV. Thus, blood flow from the pulmonary veins LUPV, LLPV, RUPV, RLPV readily passes or flows through the respective opening 46, 48 and into the interior region 30 for interaction with the prosthetic valve 24. Depending upon an operational state of the prosthetic valve 24, blood flow at the interior region 30 is either prevented or allowed through or at the lower opening 44. With embodiments in which the retention body 22 includes a liner or cover, the liner or cover can effectively close the left atrial appendage LAA.

Figure 3B:
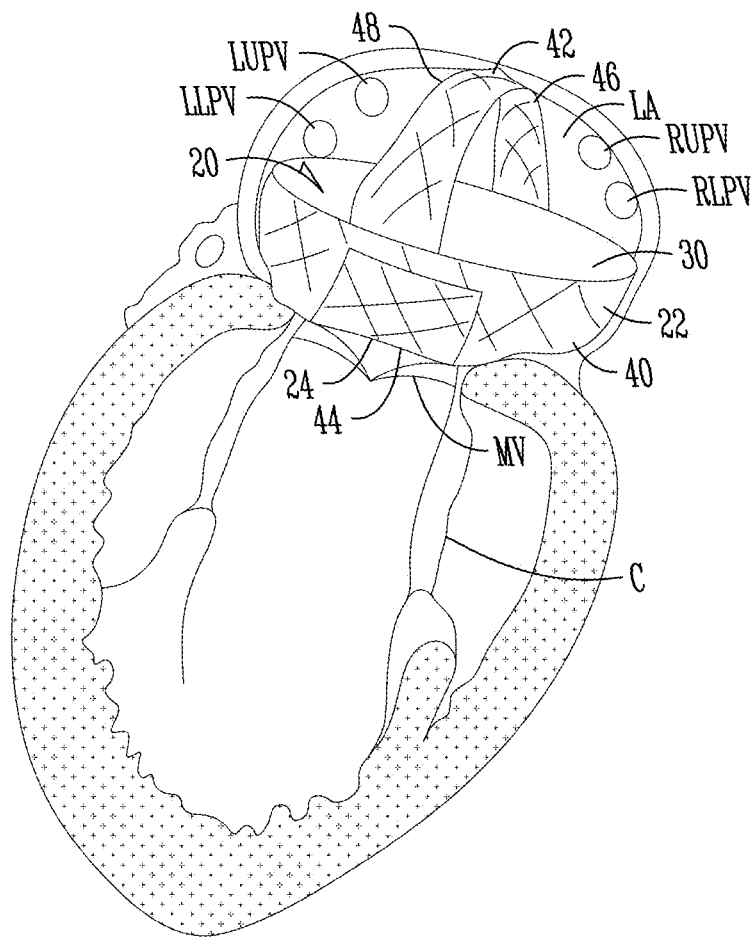
FIG. 3B is another simplified view of one arrangement of a device implanted within a left atrium portion of the anatomy of FIGS. 2A and 2B in accordance with principles of the present disclosure.

With the exemplary arrangement of FIG. 3A, the prosthetic valve 24 is disposed or implanted within the native mitral valve MV, effectively pinning the native leaflets LF open. The prosthetic valve 24 thus replaces the native mitral valve MV. In the alterative arrangement of FIG. 3B, the device 20 is configured (e.g., shaped and sized) so as to locate the prosthetic valve 24 slightly spaced from (e.g., above relative to the orientation of FIG. 3B) the native mitral valve MV upon final implant. The native mitral valve MV remains functional, with the prosthetic valve 24 serving to supplement the native mitral valve MV (e.g., with the arrangement of FIG. 3B, the prosthetic valve 24 can assist in treating various maladies such as mitral regurgitation by obstructing blood leaking through the native mitral valve MV).

Regardless of an arrangement of the prosthetic valve 24 relative to the native mitral valve MV, with optional embodiments in which the retention body 22 includes a liner, the liner can prevent the formation of blood clots along the interior surface of the left atrium LA. In light of the thin wall nature of the retention body 22, a volumetric capacity of the left atrium LA is very minimally reduced due to the presence of the device 20.

Figure 4A:
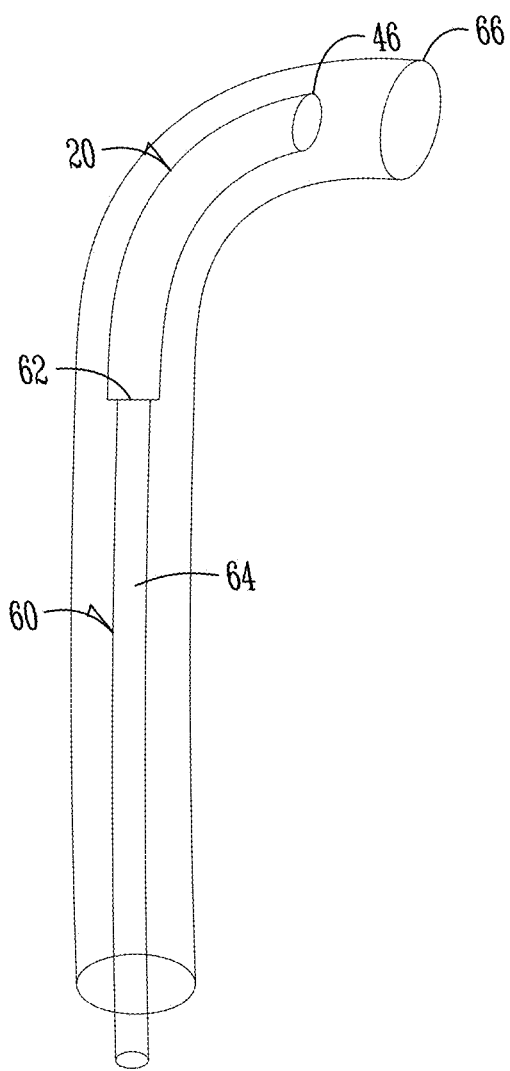
FIGS. 4A-4E illustrate a method of implanting a device of the present disclosure within the left atrium in accordance with methods of the present disclosure.

In some embodiments, the device 20 is surgically delivered to the left atrium LA. For example, the liner device 20 can be delivered by a catheter or sheath via a central artery (e.g., femoral artery, internal jugular or subclavian veins, etc.) vein with a transseptal puncture or in a retrograde fashion through the aortic and mitral valves via an arterial approach. With catheter-based delivery techniques, the device 20 is initially forced to the collapsed state shown generally in FIG. 4A and slidably inserted within a delivery catheter 60. A proximal end 62 of the device 20 is attached to an insertion tool 64 that is similarly slidably disposed within the delivery catheter 60. As a point of reference, in the collapsed state of FIG. 4A, the first opening 46 can serves as the distal end of the device 20 relative to the insertion tool 64, and is located proximal a distal end 66 of the delivery catheter 60. Thus, it is contemplated that the implant device 20 be positioned in a percutaneous manner.

Figure 4B:
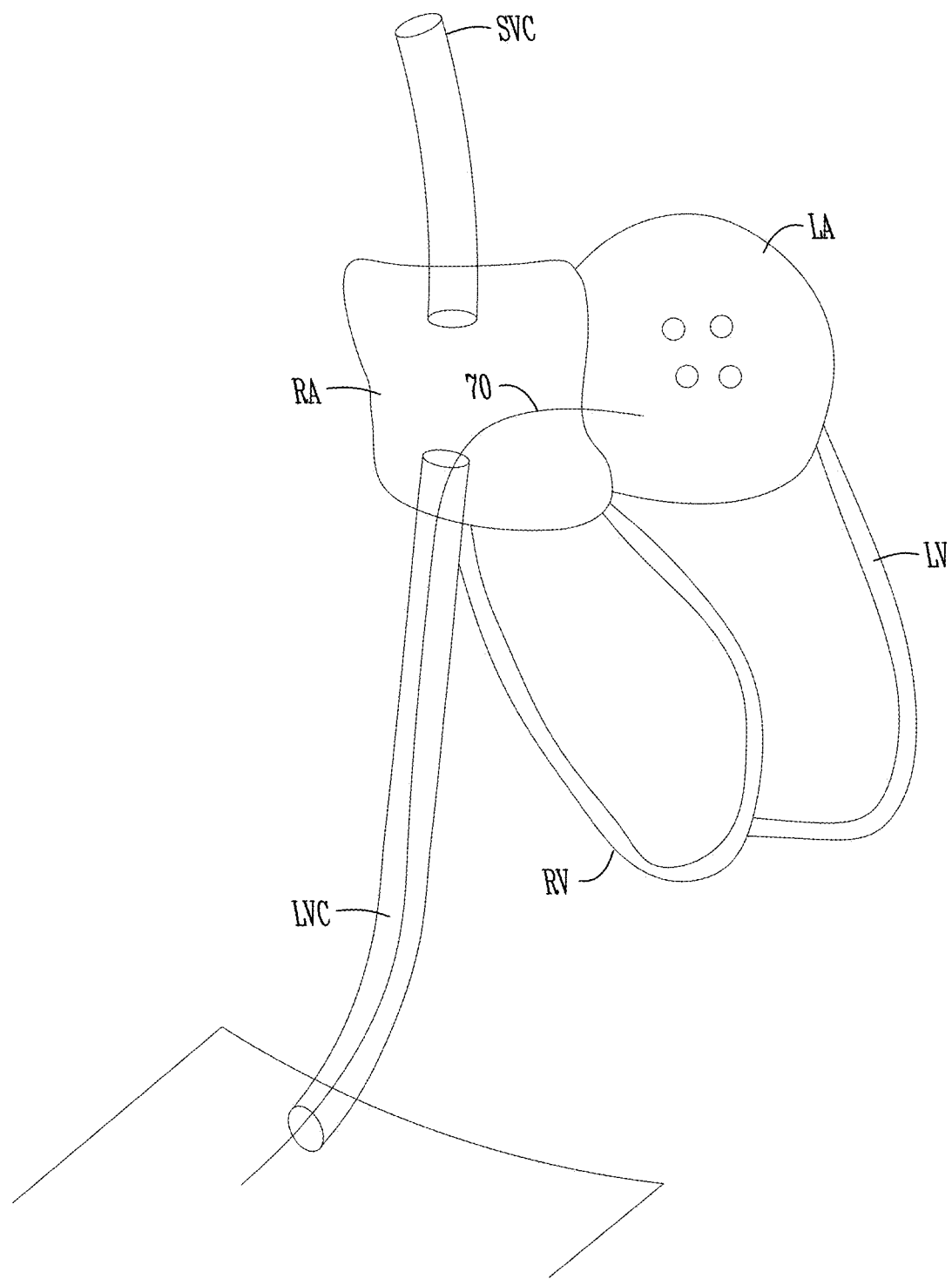
Figure 4C:
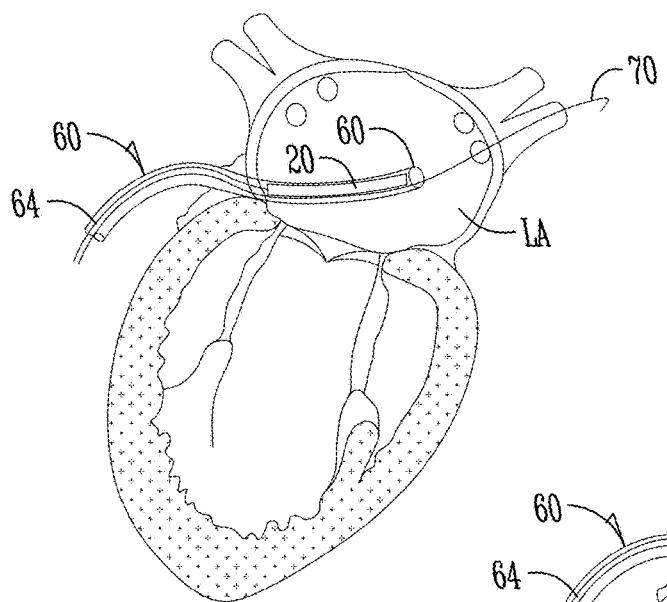

To deliver the device 20, a sheath can be placed into the right femoral vein. A transseptal puncture is done to allow a transseptal sheath to be placed across the intratrial septum and into the left atrium LA. Next, a wire 70 (or multiple wires) are placed in one (or more) of the pulmonary veins via the transseptal sheath as shown in FIG. 4B. The positioning wire or wires 70 are threaded through the pulmonary vein(s) and into the left atrium LA. With cross-reference between FIGS. 4A and 4B, the device 20 is then loaded in the transseptal delivery catheter 60 as described above, including releasably connecting the device 20 to the insertion tool 64. With the device 20 in the collapsed state, the delivery catheter 60 is then delivered through the transseptal sheath and into the left atrium LA as in FIG. 4C. With the distal end 66 of the delivery catheter 60 in the left atrium LA, the device 20 can then be released.

Figure 4D:
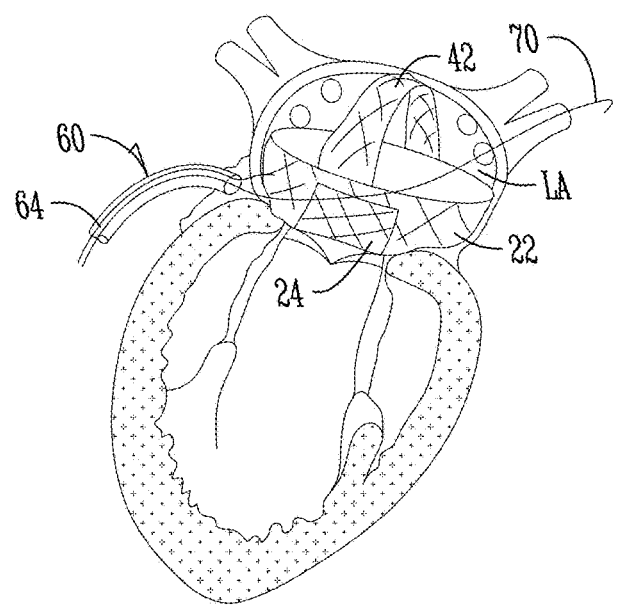
Figure 4E:
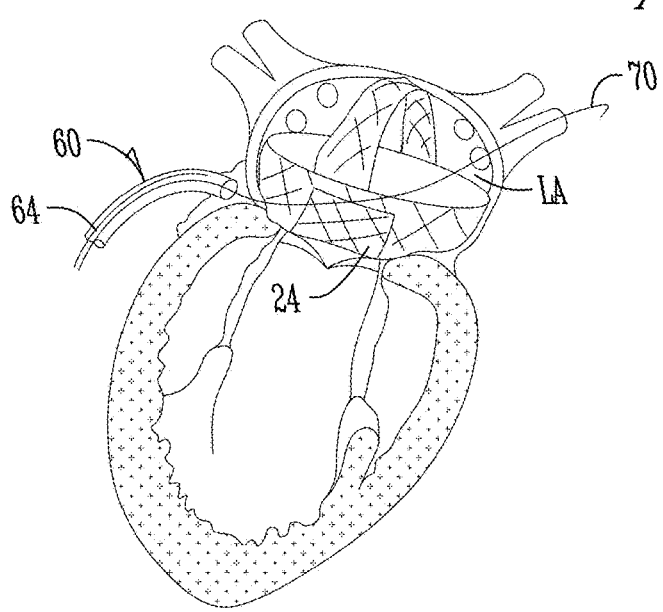

The delivery catheter 60 is retracted to deploy the device 20 as reflected by FIG. 4D. The device 20 remains attached to the insertion tool 64 and can be pulled back into the delivery catheter 60 if prepositioning of the device 20 is desired. The wire(s) 70 can then be removed. Once the device 20 is in the proper position, the insertion tool 64 is detached (e.g., via any connection structure or mechanism as known in the art, such as a threaded connection) as generally shown in FIG. 4E.

Other implant techniques are also acceptable. For example, an open heart surgical approach can be employed that optionally permits suturing of the device 20 to the native anatomy.

Figure 5:
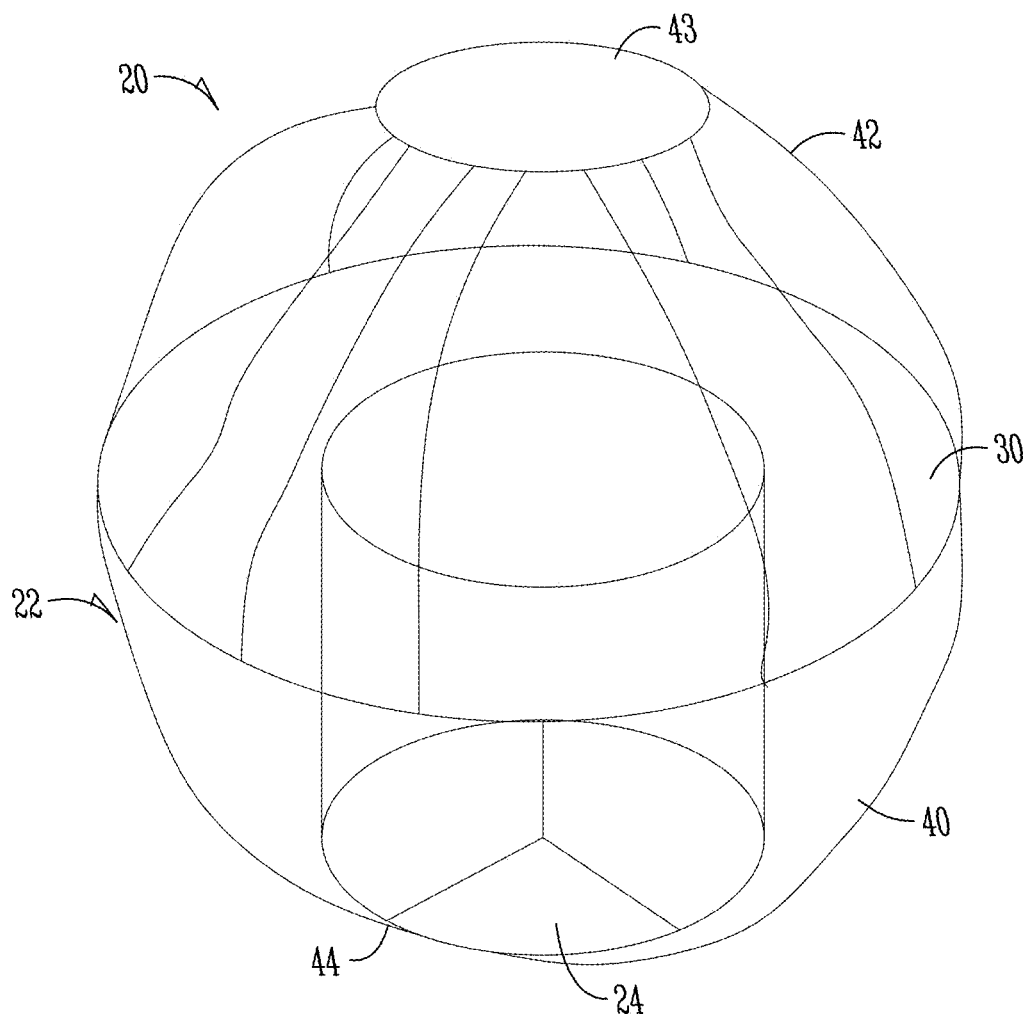
FIG. 5 is a perspective view of another implantable device in accordance with principles of the present disclosure and configured for implantation within a left atrium.
Figure 6:
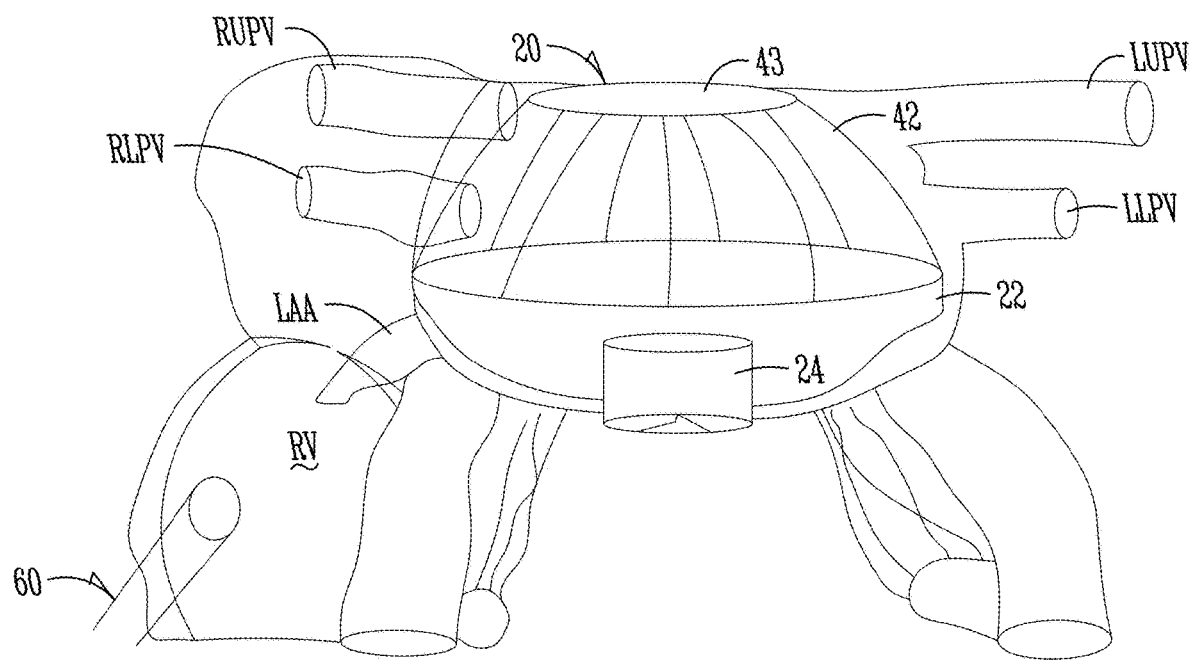
FIG. 6 is a perspective view of another implantable device implanted within a left atrium portion of a heart.

FIGS. 5 and 6 illustrate further aspects of an implant device 20 according to aspects of the disclosure. For example, the device 20 as shown in perspective view in FIG. 5 and positioned within a LA in FIG. 6 is similar to that previously disclosed. However, in the configuration of FIGS. 5 and 6, the device includes an upper support member 43 operatively attached to the retention body 22 via one or more support members 42, which generally replace the shoulder as previously disclosed. The support members 42 give the device a greater ability to expand and contract, such as during normal movements of a patient. The support members 42 can comprise a compliant material, spring or spring-like material, shape memory material, smart material or other configuration to allow for the distance between the upper support member 43 and the retention body 22 to vary during day-to-day use of the device 20. This will aid in mitigating movement of the device 20 during use so that the prosthetic valve 24 stays generally in position relative to the native mitral valve of the patient. Furthermore, as shown best in FIG. 6, the upper support member 43 can be configured to be positioned at or against a wall of the left atrium to provide a type of friction fit positioning within the atrium to hold the valve in place without the use of any anchoring system or anything connected to the heart chamber.

The device 20 shown in FIGS. 5 and 6 include wire-like members as support members 42 between the upper support member 43 and the retention body 22. These wire-like members can retract and expand to press the retention body 22 and opposite upper support member 43 into opposing portions of the heart chamber to hold the device in place. However, the compliant members 42 will allow for movement, i.e., contraction, of the device. Another advantage of the configuration shown includes that the device can be used for a greater variety of sizes of heart chambers. As the height of the device is not fixed, and instead, is contractible while wanting to expand outward, the device can be positioned in a variety of heart chamber sizes, while still maintaining its position to replace or aid in the function of the mitral valve. This can provide a type of one-size-fits-most device to fit a range of atrial sizes. Still further, as the wire-like support members 42 are separate members, there are little to no impediments in the atrium, such as blocking any passages (veins, etc.).

The upper support member 43 can comprise any of the materials previously disclosed, and also can comprise nitinol loops that are bended to be flat or slightly curved to contact a wall of the atrium. This member could also be covered with a tissue or fabric, as has been disclosed.

Figure 7:
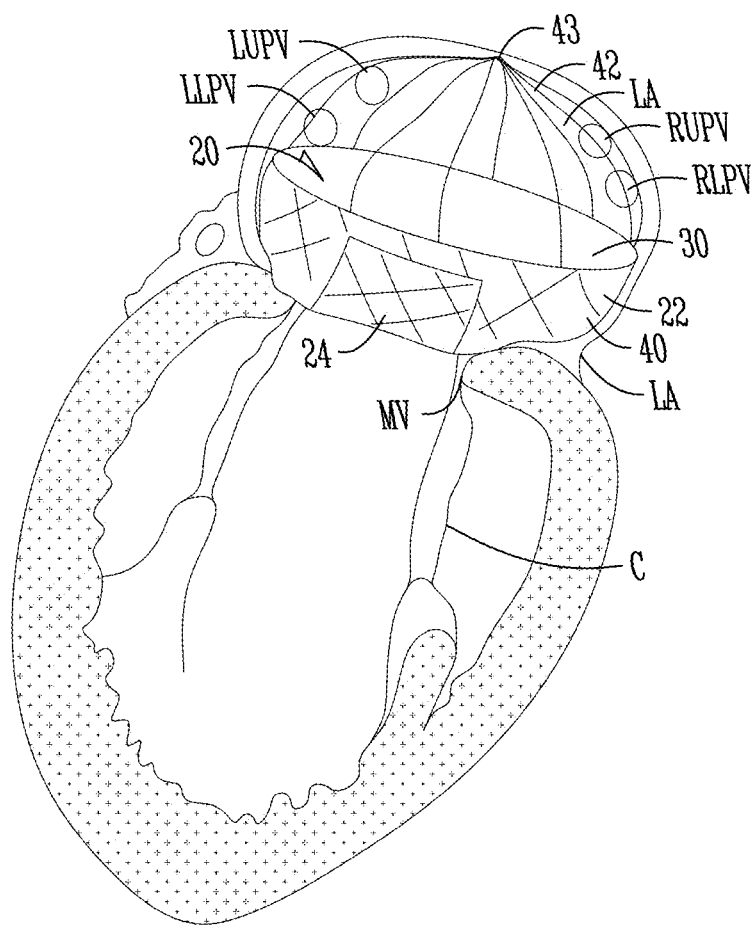
FIG. 7 is another simplified view of one arrangement of a device implanted within a left atrium portion of the anatomy of FIGS. 2A and 2B in accordance with principles of the present disclosure.

Yet another implantable device 20 is shown as positioned within a left atrium of a patient's heart in FIG. 7. The device 20 is similar to that previously disclosed. However, the device of FIG. 7 omits any sort of structured upper support member, and instead includes an apex portion 43 wherein the support members 42 congregate at a common point. The support members 42 can comprise compliant materials, spring materials, memory materials, shape memory materials, or some combination thereof. These members 42 can extend from the retention body 22 and form a dome-like shape at the apex point 43.

The device 20 of FIG. 7 will operate similarly to that as FIGS. 5 and 6, in that the device can be collapsed until positioned in a heart chamber, wherein the compliant, spring, or shape memory material will urge the device in an expanded state against the walls of the heart chamber to hold the device in place such that the prosthetic valve can be positioned to function as needed. However, the configuration will still provide the advantages of a one-size-fits most to fit a range of atrial sizes, to allow the atrium to contract, and to hold the device 20 in place without the use of anchors or attaching means to the heart chamber walls.

Figure 8:
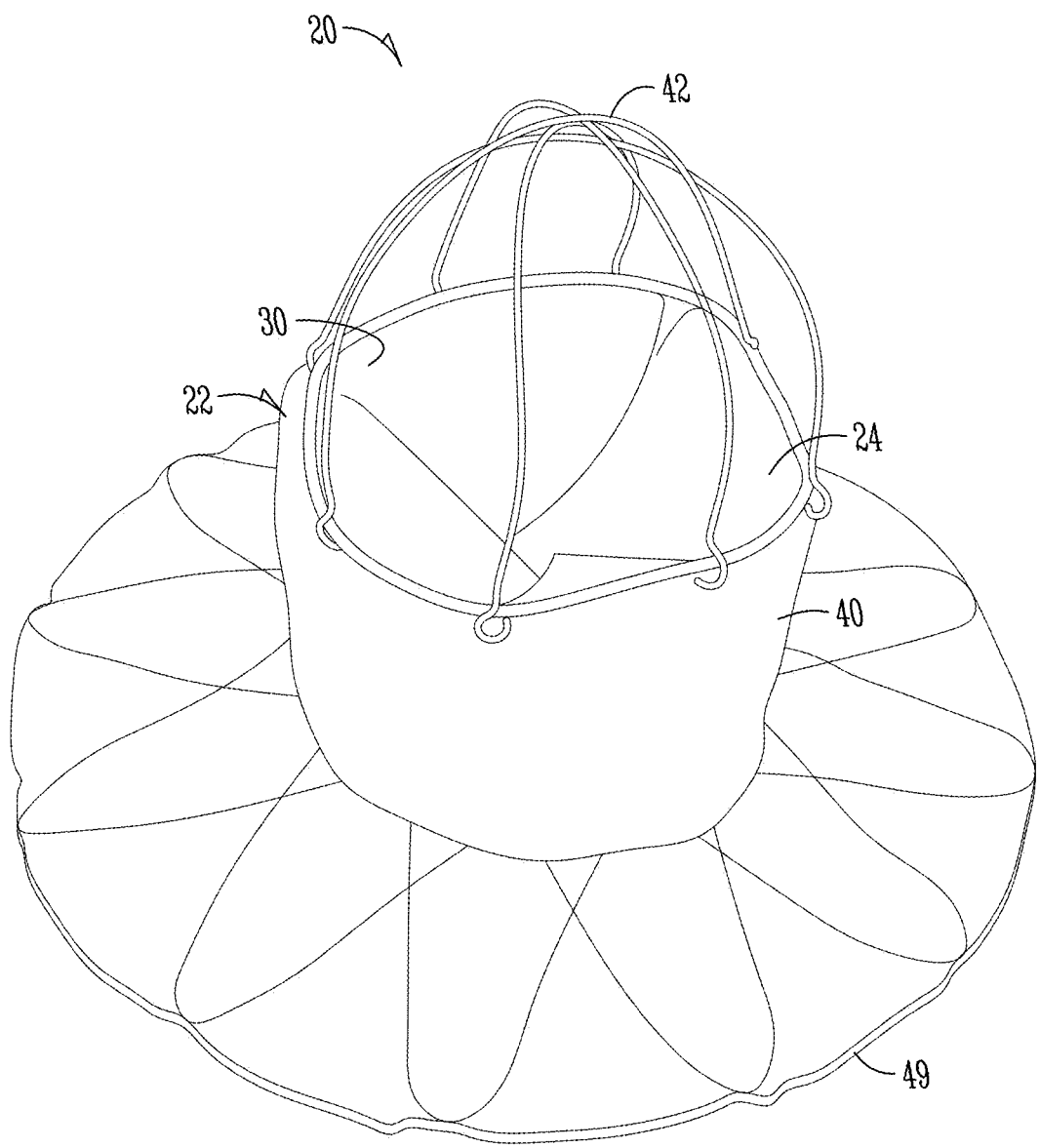
FIG. 8 is a perspective view of another implantable device in accordance with principles of the present disclosure and configured for implantation within a left atrium.

FIG. 8 shows the device 20 of FIG. 7, but with the addition of a skirt or cuff 49 extending in a flange-like manner radially from a bottom edge of the retention body 22. The skirt 49 can contact the atrial tissue to mitigate and/or prevent perivalvular leak. The skirt 49 can be an amount of material similar to the material of the retention body 22, can also include support members 42, such as those extending from the retention body. The material can be covered with tissue or other materials, as has been disclosed herein. The cuff 49 could also comprise a parachute material that can expand to collect blood, a felt or felt-like material, or other tissue that is used in heart repair, replacement, and other procedures. The cuff 49 can be integral with the retention body 22 or else permanently or temporarily affixed to the retention body at an upper or lower position, or some position in between. The support members 42 can be positioned on a side of the skirt 49 or even between two or more layers of material comprising the skirt to provide lateral support for the skirt 49 and to include a shape and/or structural memory to hold the skirt in place.

Note that it is contemplated that, while the skirt 49 is shown with the configuration of FIG. 8, it is contemplated that the skirt could be added to any of the implantable devices 20 of the present disclosure.

Figure 9:
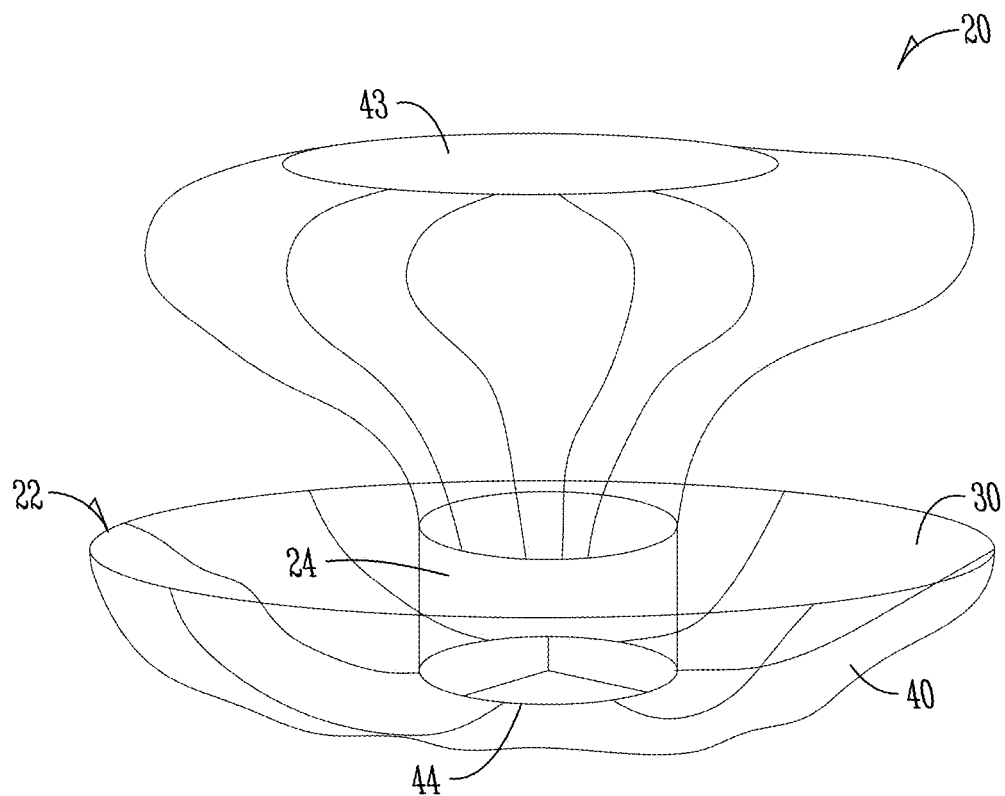
FIG. 9 is a perspective view of another implantable device in accordance with principles of the present disclosure and configured for implantation within a left atrium.
Figure 10:
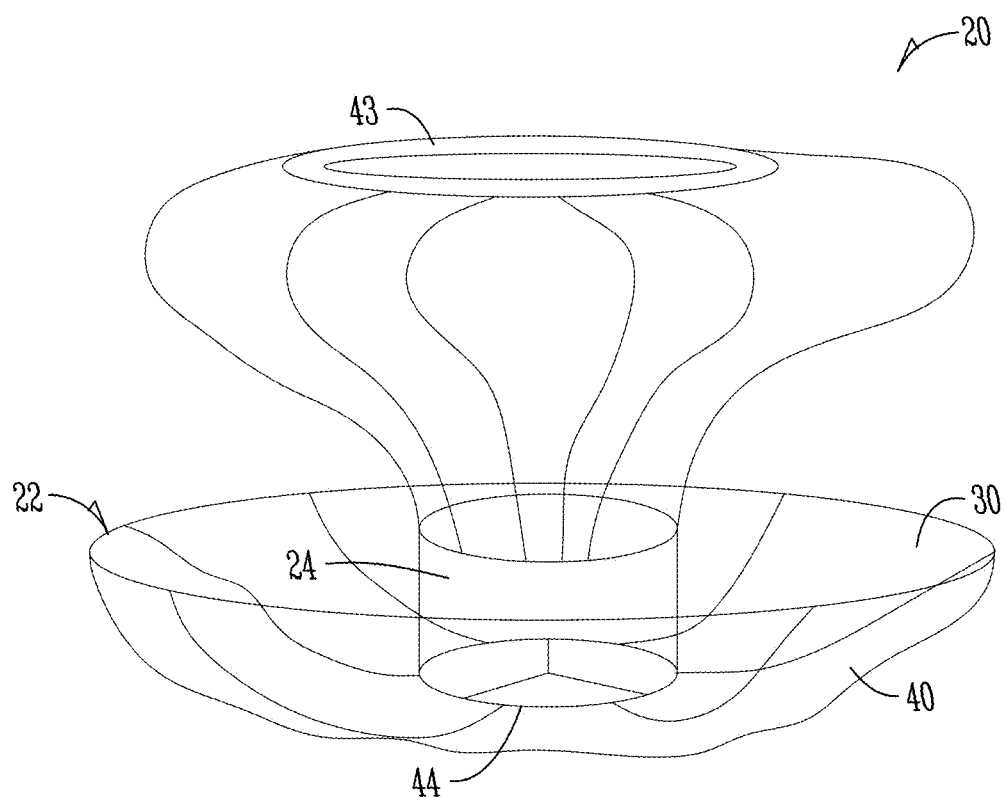
FIG. 10 is a perspective view of another implantable device in accordance with principles of the present disclosure and configured for implantation within a left atrium.
Figure 11:
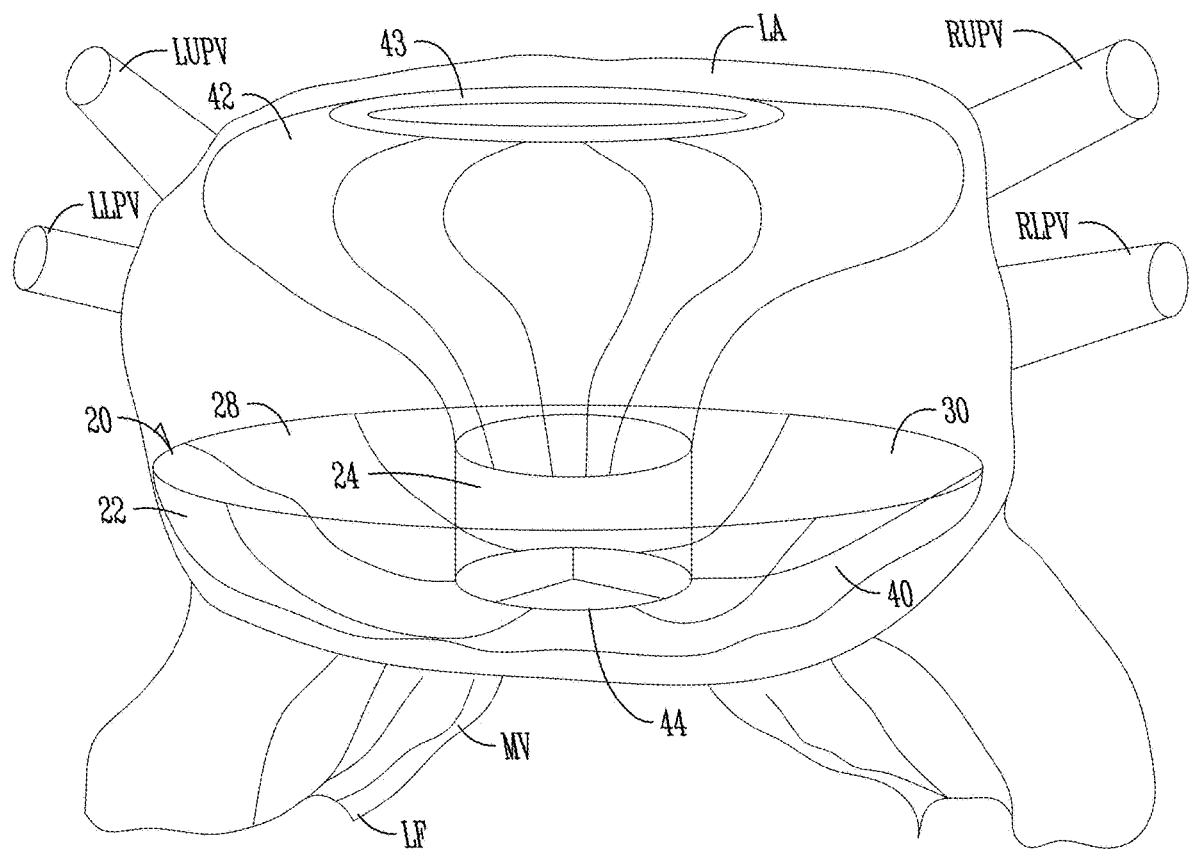
FIG. 11 is a view of the device of FIG. 10 positioned within a chamber of a patient's heart according to aspects of the invention.

FIGS. 9-11 show yet additional aspects of devices 20 according to the disclosure. For example, the configurations of FIGS. 9-11 show devices 20 with an upper support member 43 that is connected to a prosthetic valve 24 by the support members 42. The device 20 still includes a retention body 22, which can include a memory material that urges the body 22 towards a shape as shown in the figures to be positioned within a heart chamber, such as a left atrium. The valve 24 is positioned at an aperture 40 thereof, and generally within an interior 30 of the body 22. However, the support members 43, which can comprise compliant materials, spring-like wires, springs, or other memory shape materials, extend from the valve 24 to the upper support member 43. The upper support member 43, in FIG. 9, comprises a closed top. As shown in FIGS. 10-11, the upper support and/or top 43 is an open top in the form of a ring or ring-like member. Both the closed and open top members 43 could be made of nitinol loops that are bended to be flat or slightly curved to contact the roof of the atrium. The top 43 could be covered with tissue or fabric.

However, the advantages of the contraction and expansion properties of the device 20 as has been disclosed remain for this configuration as well. This includes the one-size-fits-most applicability, the ability of allowing the atrium to contract, and also to provide the forces necessary to hold the device 20 in place without the need for extra anchors or attachments to the tissues of the heart. This further allows for the atrium to remain substantially open so as to mitigate blocking of functions of the heart. Still further, the configuration can include the skirt 49 as previously disclosed, to aid in mitigating leakage, such as perivalvular leaks.

Figure 12A:
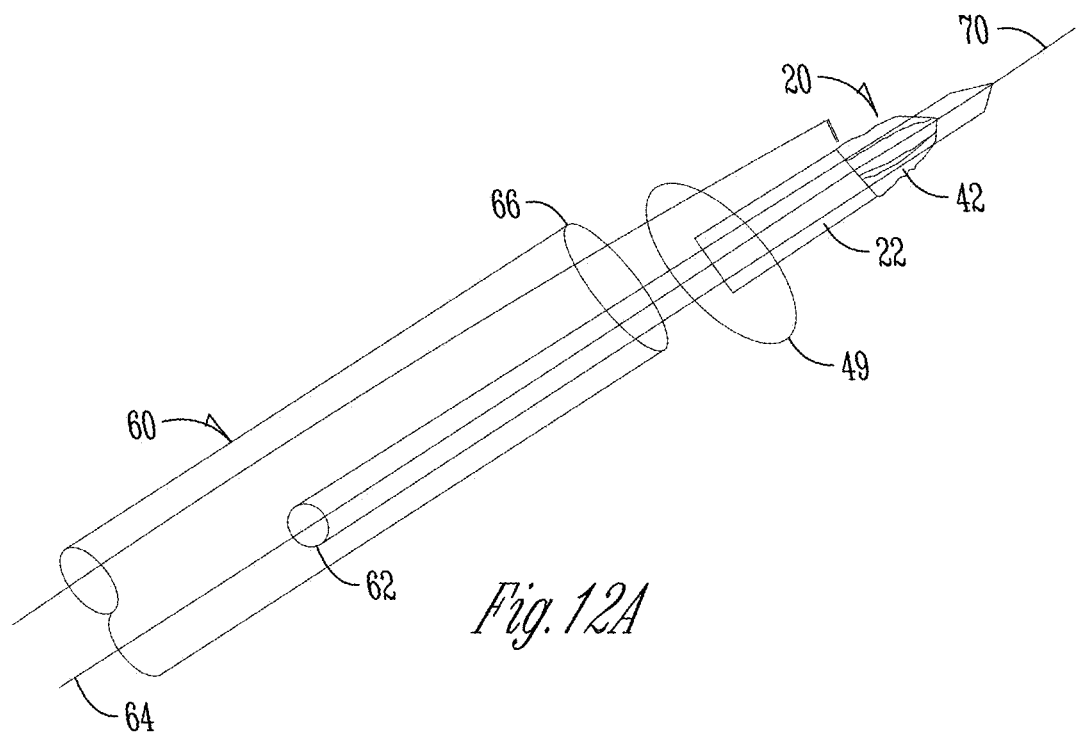
FIG. 12A is a perspective view of a delivery assembly for implanting a device into a heart chamber of a patient according to aspects of the present disclosure.
Figure 12B:
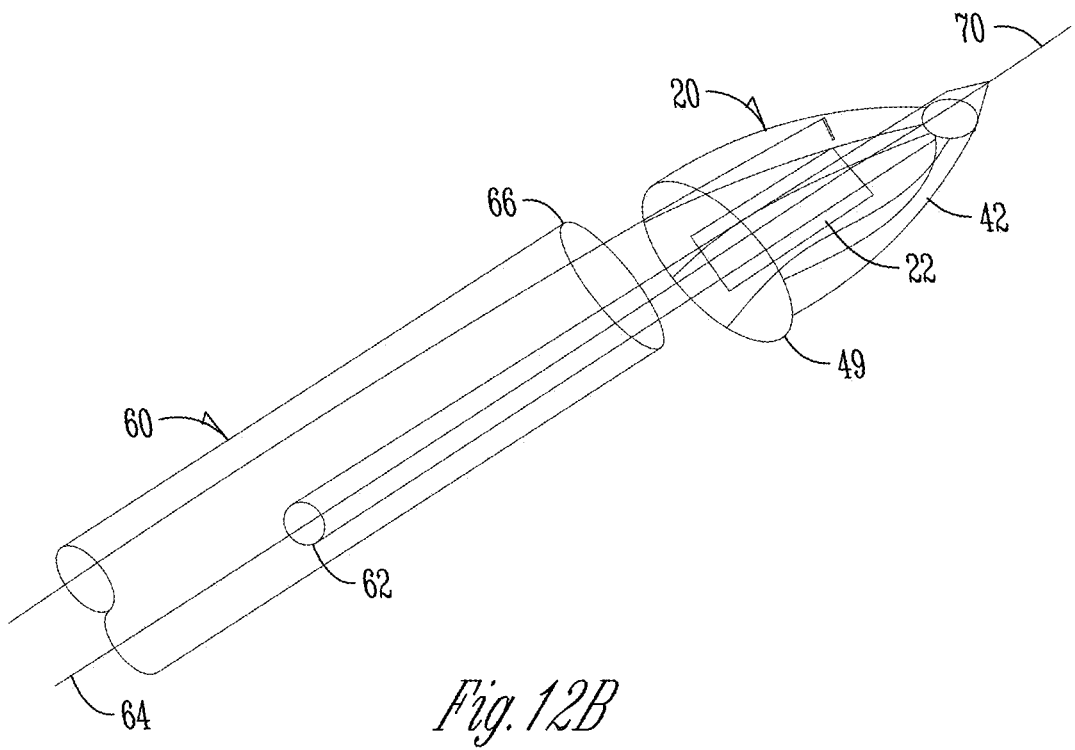
FIG. 12B is a perspective view of another delivery assembly for implanting a device into a heart chamber of a patient according to aspects of the present disclosure.

FIGS. 12A and 12B show additional configurations of the various types and configurations of implantable devices 20 of the disclosure in assembly form with a delivery catheter 60. Any and all of the devices 20 as shown and/or described, both explicitly and inherently, can be collapsed to be placed within a delivery catheter 60. This includes devices 20 including a skirt 49, as is shown in FIG. 12A, and having support members 42 extending around the retention body 22, as is down in FIG. 12B. The delivery catheter 60 and device 20 comprise a delivery assembly that can be used to position the collapsed device 20 in or at a patient's heart chamber, where it can be released to expand to a state that positions the device in the chamber while being urged in a manner to hold the device in place within the chamber without the need for anchoring or any attachment mechanisms.

As previously disclosed, the repair assembly can be moved through a vein to a location within a heart chamber with the use of wires 70 or other positioning members. The wires can then be used to remove the device 20 from the catheter 60 to allow the device to expand to a configuration within the chamber. Having one or more components of the device 20 comprising the spring, compliant, or other shape-memory material will urge the device into contact with one or more walls of the chamber to hold the device in place therein. As disclosed, this will also allow the device to be a one-size-fits-most variety, as the outwardly urging portions of the device can be configured to fit within a number of chamber sizes and/or shapes to hold the device in place to aid and/or replace the valve, to mitigate leakage, and to provide for normal heart functions.

The devices, members, assemblies, and/or methods as shown and described provide numerous advantages, on top of those disclosed herein. For example, the device can be implanted in a fully percutaneous manner, can be an all venous implant that is easy to deploy, can anchor in place such that there is little to no movement or embolizing (beyond the contracting/expanding due to normal movements of the patient or heart), and can mitigate perivalvular leak.

The device according to the aspects of the disclosure utilizes atrial anchoring, which holds position without barbs to minimize risk of perforation. This also prevents embolization, can include a skirt or cuff to mitigate the perivalvular leak, and does not interfere with chordal apparatus. This is done with substantially total atrial support only, and can be done in the full atrium. Still other advantages obvious to those skilled in the art should be appreciated.

The devices, systems and methods of the present disclosure provide a marked improvement over previous designs. The device comprises a dynamic anchoring system that allows for expanding and contracting of the device to work with the movement of a patient. The stent retention body engages with a substantial surface area of the heart chamber (e.g., left atrium), thereby securing the prosthetic valve relative to the native valve (e.g., native mitral valve) and preventing migration. Blood flow to the chamber is not obstructed. With optional embodiments in which the retention body includes a liner or cover, the left atrial appendage can be closed and/or any holes formed relative to the left atrium during delivery (e.g., hole in the intra atrial septum created by a transeptal puncture) will be closed or sealed. Also, the optional liner or covering can minimize formation of blood clots at the chamber.

Although the present disclosure has been described with reference to preferred embodiments, workers skilled in the art will recognize that changes can be made in form and detail without departing from the spirit and scope of the present disclosure. For example, while reference has been made to the device being configured for placement at the left atrium in connection with treatment of the mitral valve, in other embodiments, the device is configured (e.g., sized and shaped) for placement at a different cardiac chamber in connection with treatment of a different native valve.

What is claimed is:

1. A device for implantation within a heart chamber with a size and shape defined by at least a roof and walls and having a size and shape, the chamber in operational communication with a native valve having leaflets and an annulus, the device comprising:
   a retention body comprising an expandable and collapsible stent defining an interior, a first side and a second side and comprising:
   a base section having an outer surface and an inner surface, wherein the outer surface of the base section comprises a lowermost surface of the device;
   an opening disposed at the first side of the retention body;
   at least one support member attached to the second side of the retention body opposite the first side;
   an upper support member top attached to the at least one support member that, when implanted, is in contact with the roof of the chamber, the at least one support member biased to press the upper support member top against the heart chamber roof; and
   a prosthetic valve comprising a plurality of prosthetic leaflets, wherein the prosthetic valve is disposed entirely within the interior of the base section and proximate the opening disposed at the first side of the retention body such that the prosthetic valve is spaced above the lowermost surface of the device,
   wherein the device, when implanted in the heart chamber, is configured to be retained completely within the heart chamber and wherein the prosthetic valve is spaced away from the native valve.

2. The device of claim 1, wherein the retention body is arranged to achieve at least one biased expanded state and a collapsed state, the at least one biased expanded state comprising a retention body size and shape that conforms with the size and shape of the heart chamber.

3. The device of claim 2, wherein the upper support member top is urged against the roof of the heart chamber, the first side of the retention body is urged against the annulus, and the base section is urged against the walls of the heart chamber and thereby hold the expanded device in position within the chamber only by a combination of pressured and frictional fit positioning.

4. The device of claim 1, wherein the upper support member top is a closed ring-like structure.

5. The device of claim 4, wherein the closed ring-like structure comprises at least one of the group consisting of: a compliant material, and a non-compliant material.

6. The device of claim 5, wherein the closed ring-like structure comprises a memory shape material.

7. The device of claim 6, wherein the memory shape material comprises nitinol formed into loops.

8. The device of claim 5, wherein the closed ring-like structure comprises nitinol.

9. The device of claim 8, wherein the ring-like upper support member top is an open structure.

10. The device of claim 4, further comprising a covering over the closed ring-like structure.

11. The device of claim 10, wherein the covering comprises at least one of the group consisting of: tissue and fabric.

12. The device of claim 1, wherein the upper support member top is an open structure.

13. The device of claim 12, wherein the open structure comprises a compliant material.

14. The device of claim 13, wherein the open structure comprises a memory shape material.

15. The device of claim 14, wherein the open structure comprises nitinol.

16. The device of claim 14, wherein the memory shape material comprises nitinol formed into loops.

17. The device of claim 14, wherein the covering comprises at least one of the group consisting of: tissue and fabric.

18. The device of claim 16, wherein the open structure consists of one of a compliant and a non-compliant material.

19. The device of claim 12, wherein the open structure is covered by at least one of the group consisting of: tissue and fabric.

20. The device of claim 19, wherein the open structure comprises a memory shape material.

21. The device of claim 20, wherein the open structure is covered by at least one of the group consisting of: tissue and fabric.

22. The device of claim 1, wherein the base section comprises an expanding compliant material.

23. The device of claim 22, wherein the open structure comprises nitinol.

24. The device of claim 22, wherein the memory shape material comprises nitinol formed into loops.

25. The device of claim 1, further comprising a liner over the base section.

26. The device of claim 1, the retention body comprising a shape memory material.

27. The device of claim 26, wherein the shape memory material comprises nitinol.

28. The device of claim 1, the retention body further comprising expanding biased springs.

29. The device of claim 1, wherein at least the outer surface of the base section comprises a liner.

30. The device of claim 29, wherein the liner comprises at least one of the group consisting of: a fabric, a polymer, a metal mesh, braided material, amnion tissue, placental tissue, pericardium tissue, small intestine tissue, and an anti-thrombotic material.

31. The device of claim 29, wherein the liner is in direct, intimate and sealed contact with the walls.

32. The device of claim 1, further comprising a skirt attached to the base section proximate the opening and extending radially outwardly around the base section.

33. The device of claim 1, further comprising a skirt attached to the base and extending radially outwardly around the base section.

34. A device for implantation within a patient's left atrium having a size and shape defined by at least an atrial roof and walls and an annulus of a native mitral valve, the device comprising:
  a retention body comprising an expandable and collapsible stent defining an interior, a first side and a second side and comprising:
  an expandable and collapsible base section having an outer surface comprising a lowermost surface of the device;
  a lower opening disposed at the first side of the retention body;
  at least one support member attached to the second side of the retention body opposite the first side;
  a ring-like upper support member top attached to the at least one spring support member that, when implanted, is in contact with the atrial roof, the at least one support member biased to press the ring-like upper support member top against the atrial roof; and
  a prosthetic valve comprising a plurality of prosthetic leaflets, wherein the prosthetic valve is disposed entirely within the interior of the base section and proximate the lower opening such that the prosthetic valve is spaced above the lowermost surface of the device;
  the retention body arranged to achieve at least one biased expanded state and a collapsed state, the at least one biased expanded state comprising a retention body size and shape that conforms with the size and shape of the left atrium, and
  wherein the ring-like upper support member top is urged against the atrial roof of the left atrium, the first side of the retention body is urged against the mitral valve annulus, and the base section is urged against the walls of the left atrium and thereby are configured to hold the expanded device in position within the chamber only by a combination of pressured and frictional fit positioning,
  wherein, when expanded within the left atrium, the device is configured to be completely retained within the left atrium and wherein the prosthetic valve is configured to be spaced above the native mitral valve.

35. The device of claim 34, wherein the ring-like upper support member top is a closed structure.

36. The device of claim 35, wherein the closed structure consists of one of a non-compliant and a compliant material.

37. The device of claim 35, wherein the closed structure comprises a memory shape material.

38. The device of claim 37, wherein the memory shape material comprises nitinol formed into loops.

39. The device of claim 35, wherein the closed structure comprises nitinol.

40. The device of claim 34, further comprising a covering over the closed structure.

41. The device of claim 34, wherein the base section comprises an expanding compliant material.

42. The device of claim 34, further comprising a liner over the base section.

43. The device of claim 34, the retention body comprising a shape memory material.

44. The device of claim 34, wherein the shape memory material comprises nitinol.

45. The device of claim 34, the retention body comprising expanding springs.

46. The device of claim 34, wherein at least part of the outer surface of the base section comprises a liner.

47. The device of claim 46, wherein the liner comprises at least one of the group consisting of: a fabric, a polymer, a metal mesh, braided material, amnion tissue, placental tissue, pericardium tissue, small intestine tissue, and an anti-thrombotic material.

48. The device of claim 47, wherein the liner is in direct, intimate and sealed contact with the atrial walls.

49. The device of claim 48, wherein the outer surface of the base section is configured to be in covered and sealed engagement over the left atrial appendage located in the left atrium.

50. The device of claim 34, further comprising a skirt attached to the base proximate the lower opening and extending radially outwardly around the base section.

* * * * *